United States Patent
Roehm et al.

(10) Patent No.: US 8,827,905 B2
(45) Date of Patent: Sep. 9, 2014

(54) PATIENT INITIATED ON-DEMAND REMOTE MEDICAL SERVICE WITH INTEGRATED KNOWLEDGE BASE AND COMPUTER ASSISTED DIAGNOSING CHARACTERISTICS

(75) Inventors: Steven Roehm, Waukesha, WI (US); Ray Liu, Milwaukee, WI (US); Gopal B. Avinash, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 1873 days.

(21) Appl. No.: 11/324,911

(22) Filed: Jan. 4, 2006

(65) Prior Publication Data

US 2007/0156626 A1     Jul. 5, 2007

(51) Int. Cl.
| | |
|---|---|
| *G11B 20/00* | (2006.01) |
| *G11B 27/36* | (2006.01) |
| *G11B 20/18* | (2006.01) |
| *A61B 5/02* | (2006.01) |
| *A61B 5/00* | (2006.01) |
| *G06F 19/00* | (2011.01) |

(52) U.S. Cl.
CPC .................. *A61B 5/0002* (2013.01); *A61B 5/02* (2013.01); *G06F 19/3487* (2013.01); *G06F 19/345* (2013.01); *G06F 19/3425* (2013.01); *G06F 19/3406* (2013.01); *A61B 5/74* (2013.01); *A61B 2505/07* (2013.01); *G06F 19/3412* (2013.01); *G06F 19/3418* (2013.01); *Y10S 706/924* (2013.01); *Y10S 706/902* (2013.01); *Y10S 128/92* (2013.01); *Y10S 128/903* (2013.01)
USPC .......... 600/301; 706/924; 706/902; 369/53.1; 128/920; 128/903; 705/2; 705/3; 340/539.12

(58) Field of Classification Search
USPC .................. 600/300, 301; 128/903–905, 920
See application file for complete search history.

(56) References Cited

U.S. PATENT DOCUMENTS

| | | | |
|---|---|---|---|
| 5,710,759 A | 1/1998 | Chopping et al. | |
| 6,213,942 B1 * | 4/2001 | Flach et al. | 600/300 |
| 6,302,844 B1 * | 10/2001 | Walker et al. | 600/300 |
| 6,336,900 B1 * | 1/2002 | Alleckson et al. | 600/485 |
| 6,364,834 B1 * | 4/2002 | Reuss et al. | 600/300 |

(Continued)

FOREIGN PATENT DOCUMENTS

| | | | |
|---|---|---|---|
| WO | 02071305 a2 | 9/2002 | |
| WO | 03043494 | 5/2003 | |
| WO | 2004/090661 A2 | 10/2004 | |
| WO | WO 2005114524 A2 * | 12/2005 | G06F 17/60 |

OTHER PUBLICATIONS

International Search Report mailed Jan. 10, 2008.
Lu, Hsi-Feng et al. (2005) "Design of a residental gateway for tele-homecare systems" Consumer Electronics, 2005. (ISCE 2005). Proceedings of the Ninth International Symposium on Macau Sar Jun. 14-16, 2005, Piscataway, NJ, USA, IEEE, pp. 291-295.

(Continued)

*Primary Examiner* — William Thomson
*Assistant Examiner* — Marie Archer
(74) *Attorney, Agent, or Firm* — Andrus Intellectual Property Law, LLP

(57) ABSTRACT

The present invention is a system and method of remote patient monitoring to allow a patient to initiate and activate sensing systems. In the system and method, standard parameters can be sensed, and the information can then be processed and sent to the physician or clinician. The clinician then has the ability to remotely configure or reconfigure the parameters of the sensing system so as to probe for more targeted information based on the initial sensed data.

19 Claims, 5 Drawing Sheets

(56) References Cited

U.S. PATENT DOCUMENTS

| | | |
|---|---|---|
| 6,416,471 B1 * | 7/2002 | Kumar et al. ............... 600/300 |
| 6,497,655 B1 * | 12/2002 | Linberg et al. ............. 600/300 |
| 6,569,094 B2 * | 5/2003 | Suzuki et al. ............... 600/300 |
| 7,547,278 B2 * | 6/2009 | Miyazaki et al. ........... 600/300 |
| 8,255,238 B2 * | 8/2012 | Powell et al. .................... 705/3 |
| 2002/0077801 A1 * | 6/2002 | Morehead et al. ............ 703/24 |
| 2002/0082867 A1 * | 6/2002 | MacCarter et al. ............ 705/2 |
| 2003/0069752 A1 * | 4/2003 | LeDain et al. .................. 705/2 |
| 2003/0130590 A1 | 7/2003 | Bui et al. |
| 2004/0122489 A1 | 6/2004 | Mazar et al. |
| 2004/0127775 A1 | 7/2004 | Miyazaki et al. |
| 2005/0038674 A1 * | 2/2005 | Braig et al. ..................... 705/2 |
| 2005/0101843 A1 | 5/2005 | Quinn et al. |
| 2006/0036134 A1 * | 2/2006 | Tarassenko et al. ......... 600/300 |
| 2006/0122864 A1 | 6/2006 | Gottlesman et al. |
| 2006/0178914 A1 * | 8/2006 | Brown .............................. 705/3 |
| 2007/0033072 A1 * | 2/2007 | Bildirici .......................... 705/3 |
| 2007/0282177 A1 * | 12/2007 | Pilz ............................. 600/301 |

OTHER PUBLICATIONS

Cheng, Liang et al. (2004) "Integration of wireless sensor networks, wireless local area networks and the internet" Networking, Sensing and Control, 2004 IEEE International Conference on Taipei, Taiwan, Mar. 21-23, 2004, Piscataway, NJ, USA, IEEE, vol. 1, pp. 462-467.

Jovanov, Emil et al. (2005) "A wireless body area network of intelligent motion sensors for computer assisted physical rehabilitation" Journal of Neuroengineering and Rehabilitation, Biomed Central, London, GB, vol. 2, No. 1, pp. 1-6.

Krco, Srdjan (2003) "Implementation solutions and issues in building a personal sensor network for health care monitoring" Information Technology Applications in Biomedicine, 2003. 4th International IEEE EMBS Special Topic Conference on Apr. 24-26, 2003, Piscataway, NJ, USA, IEEE, pp. 350-353.

Korhonen, Ilkka et al. (2003) "Health monitoring in the home of the future" IEEE Engineering in Medicine and Biology Magazine, IEEE Service Center, Pisactaway, NJ, USA, vol. 22, No. 3, pp. 66-73.

\* cited by examiner

PATIENT INITIATED ON-DEMAND REMOTE MEDICAL SERVICE WITH INTEGRATED KNOWLEDGE BASE AND COMPUTER ASSISTED DIAGNOSING CHARACTERISTICS

FIELD OF THE INVENTION

The invention is related to the field of patient monitoring. More specifically, the invention is related to the field of remote patient monitoring.

BACKGROUND OF THE INVENTION

The ability to remotely monitor patient health characteristics greatly expands the scope of services possible for medical diagnostics and treatment. Traditional patient monitoring often requires bulky and expensive equipment specialized for each sensing parameter, so the sensing and monitoring are often limited to the hospital or clinic. Current miniaturization of this equipment has allowed for the development of mobile sensing devices, and advancements in communication technology have allowed for such devices to be monitored remotely, such as in a patient's home. This combination of the technological advancements is known as remote patient monitoring.

While remote patient monitoring currently exists to some extent, its full capabilities it have yet to be realized. Specifically, most sensing devices are able to monitor only one parameter at a time, and the information is directly sent to the monitoring center. Different sensors do not have an effective system to communicate with each other, and the processing of sensed information cannot be performed in real time with integrated information from all sensors. The result of this incompatibility is a limited set of sensing applications and a sensing system that is not adaptable to changing needs of the patient.

Also, current sensors for remote patient monitoring are still too bulky for very portable applications, and they are costly such that they are not disposable. The sensors that exist in remote patient monitoring systems today are also not autonomous, meaning that the patient must proactively turn on the sensor or apply the sensor every time information is collected.

Furthermore, the process of medical care today is a very slow and inefficient one. With the exception of emergencies, when a patient becomes sick, he or she must first call the doctor's office to schedule an appointment, which may be set for several days from the initial call. Once the appointment time rolls around, the patient must drive to the doctor's office, and is placed in queue to be examined by the nurse and doctor. The total examination time could last only a few minutes, yet the patient may still be required to wait in queue for up to several hours. Without the ability to remotely monitor a patient's condition the inefficient situation described above is difficult to avoid. Remote monitoring systems have been designed primarily for patients with chronic diseases. Therefore, they have very targeted applications and limited applicability to the standard population.

SUMMARY OF THE INVENTION

The present invention is a system and method of remote patient monitoring to allow a patient to initiate and activate sensing systems. In the system and method, standard parameters can be sensed, and the information can then be processed and sent to the physician or clinician. The clinician then has the ability to remotely configure or reconfigure the parameters of the sensing system so as to probe for more targeted information based on the initial sensed data.

One aspect of the present invention is a system for remotely monitoring patient healthcare characteristics, the system comprising a plurality of sensors configured in a home environment of a patient, and further configured to collect a set of patient health characteristics from a patient, a central hub configured in the home environment, wherein the central hub receives the set of patient health characteristics, a wireless network configured to couple the plurality of sensors and the central hub, a clinician hub coupled with the central hub, the clinician hub configured to receive a patient status from the central hub and to send the patient status to an appropriate clinician, a graphical patient interface configured to allow the patient to activate the plurality of sensors, and further configured to allow the patient to communicate with the clinician and a graphical user interface configured such that the clinician can access the clinician hub and reconfigure the central hub, and configured to allow the clinician to communicate with the patient. The size of the plurality of sensors are in a range from micro-scale to millimeter-scale. The plurality of sensors may be any of a number of sensor types including: invasive implantable; non-invasive, portable device embeddable; and, non-invasive, home device embeddable.

The clinician hub may be configured outside of the home environment. The patient status includes a report when the set of patient health characteristics is within a predetermined normal range, and the patient status including the report and an alarm when the set of patient health characteristics are not in the predetermined normal range. The central hub is further configured to evaluate the set of patient health characteristics as best, comparative or cumulative. The plurality of sensors is directly coupled with the central hub through the wireless network, or the plurality of sensors are coupled with the central hub through the wireless network in an ad-hoc fashion.

A sensing sub-system is configured to receive the set of patient health characteristics from the plurality of sensors, and further configured relay the set of patient health characteristics to the central hub. The clinician reconfigures the central hub to alter the set of patient health characteristics collected by the plurality of sensors.

Another aspect of the present invention is a method of remotely monitoring patient healthcare characteristics, the method comprising activating a plurality of sensors, wherein the plurality of sensors are activated with a graphical patient interface, collecting a set of patient healthcare characteristics from a patient with a plurality of sensors, processing the set of patient healthcare characteristics in a central hub, wherein the plurality of sensors and the central hub are configured in a home environment, and further wherein the plurality of sensors send a patient status from the central hub to a clinician hub, directing the patient status with the clinician hub to an appropriate clinician, and accessing the patient status by the clinician with a graphical user interface wherein the graphical patient interface and the graphical user interface are configured to communicate with one another. The size of the plurality of sensors are in a range from micro-scale to millimeter-scale. The plurality of sensors may be any of a number of sensor types including: invasive implantable; non-invasive, portable device embeddable; and, non-invasive, home device embeddable.

The clinician hub may be configured outside of the home environment. The patient status includes a report when the set of patient health characteristics is within a predetermined normal range, and the patient status includes the report and an alarm when the set of patient health characteristics are not in the predetermined normal range. The central hub is configured to evaluate the set of patient health characteristics as best, comparative or cumulative with the central hub and each of the plurality of sensors is directly coupled with the central hub through the wireless network, or coupled with the central hub through the wireless network in an ad-hoc fashion. The method further comprises receiving the set of patient health characteristics from the plurality of sensors with a sensing sub-system, and further comprising relaying the set of patient health characteristics to the central hub with the sensing sub-system.

DETAILED DESCRIPTION OF THE INVENTION

Figure 1:
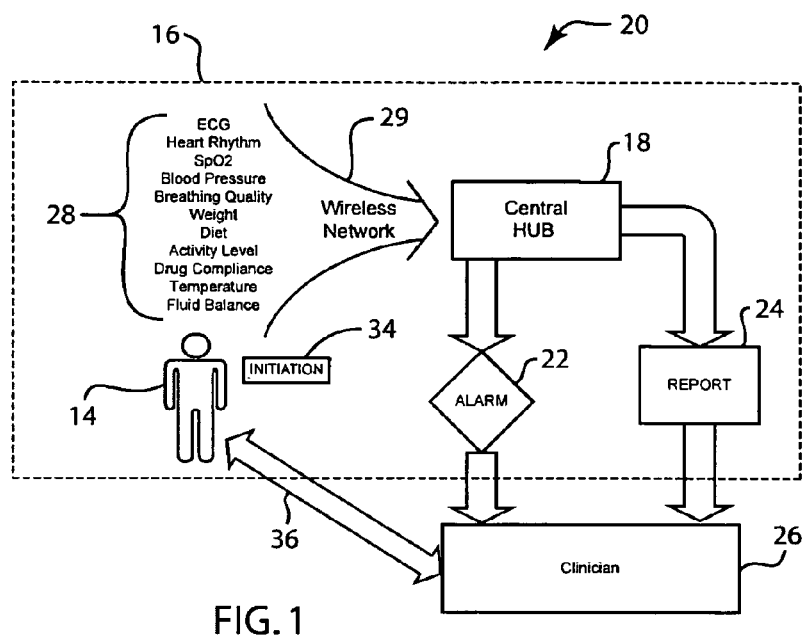
FIG. 1 illustrates a block diagram of an embodiment of the method of the present invention.

A high-level block diagram of the monitoring method 20 is depicted in FIG. 1. Here, the patient 14 utilizes the patient initiation apparatus 34 to connect the necessary sensor and activate the sensing system. The patient initiation apparatus 34 also allows the patient 14 to interact with the clinician 26. When the patient 14 connects the necessary sensors and activates the sensing system with the patient initiation apparatus 34, the appropriate patient health characteristics 28 are collected and sent along a wireless network 29 to the central hub 18. The central hub 18 processes these patient health characteristics 28, and an alarm 22 and report 24 are sent to the clinician 26. The patient/clinician interface 36 may also allow the clinician 26 to interact with the patient 14, such as to provide a response or report to the patient 14. Referring again to FIG. 1, a set of patient health characteristics 28 is collected from the patient 14 and transferred over a wireless network 29 to a central hub 18 for pre-processing. The central hub 18 is configured to report 24 to the clinician 26 when the central hub 18 receives and processes a set of patient heath characteristics 28. In the case where the central hub 18 receivers characteristics 28 outside a predetermined acceptable range for the patient 14, the alarm 22 will alert the clinician 26.

Figure 2:
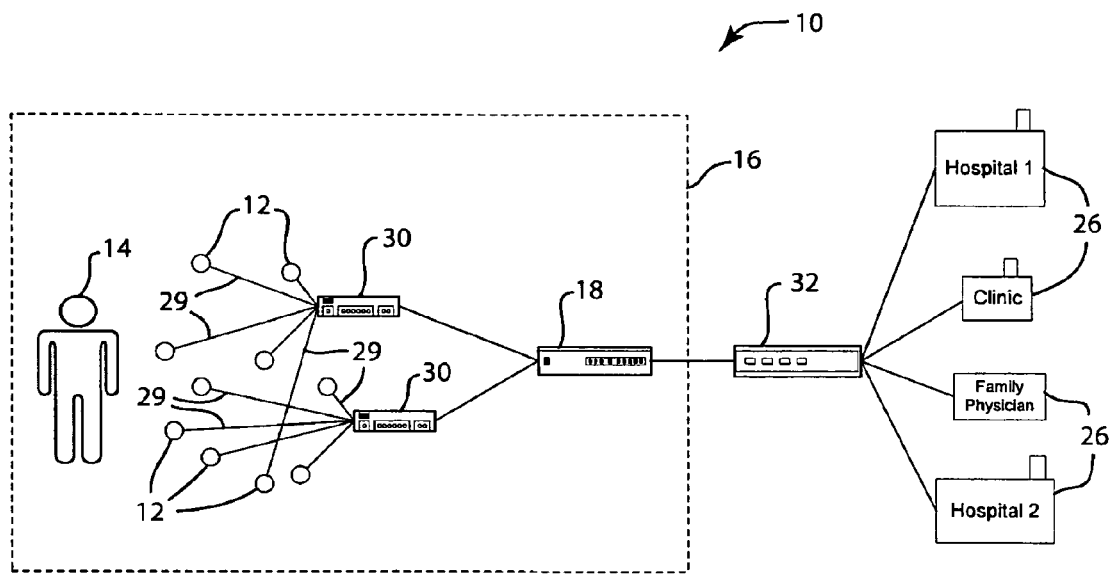
FIG. 2 illustrates a block diagram of an embodiment of the system of the present invention.

A block diagram of an embodiment the remote patient monitoring system 10 is shown in FIG. 2. The system 10 includes at least two sensors 12 to collect information from a patient 14 in a home environment 16 of the patient 14, but may have significantly more than two sensors 12. The multiple sensors 12 may collect the same information parameter from a different patient 14, different information parameters from the same patient 14, or different information parameters from different patients 14. The remote patient monitoring system 10 described may also include multiple sensing parameters, invasively implantable patient sensors 12, non-invasive embeddable, wearable sensors 12, as well as non-invasive embeddable, portable device or home device sensors 12.

The sensors 12 are preferably integrated into micro-scale to millimeter-scale devices (or smaller). Such small-scale sensors 12 bring many advantages and allow a host of new applications. One such advantage is environment sensing, wherein an indefinite number of these micro-sensors 12 is scattered into the environment to detect parameters or perturbations. Such small sensors 12 can be nearly invisible to the naked eye, and therefore do not disturb the home environment 16 in any way. Another advantage is wearable sensing, in that micro-scale sensors 12 can be applied to the surface of the patient 14 without notice to the patient 14. Yet another advantage is implantable sensing, wherein a micro-scale sensor 12 can be implanted into the patient 14 without harm or impact to the patient, and embeddable sensing, wherein a micro-scale sensor 12 can be embedded into many objects such as, but not limited to, clothing, appliances, furniture, portable devices, glasses, electronics, and home fixtures. Each sensor 12 can be embedded into a portable device of the patient 14, such as, but not limited to, a cane or walking stick, a keychain, remote control, furniture, or appliance.

In a preferred embodiment, the sensors 12 are omni sensing in that they integrate multiple sensors 12, sensing multiple parameters and data types. These sensors 12 are configured to sustain continuous communication and coordination between multiple sensors 12 and/or the central hub 18 in realtime, such that the processing of any sensed information can be performed in real time, and integrated with any other information from other sensor systems. This effective communication allows the system 10 to automatically adjust in real time. Specifically, the system 10 is able to turn specific sensors 12 on and off, modify the sensing parameters, change sensor 12 sensitivities, as well as save system 10 power, and any other system function related to the sensors 12.

Still referring to FIG. 1, the sensors 12 in the home environment 16, and the central hub 18 are constructed such that they are portable, and the sensors 12 are constructed to be disposable as well. The portable and disposable nature of the sensors 12 allows a system 10 that includes sensors 12 that are scattered in the home environment 16. This allows for relative ease in expanding or reducing the size of the home environment 16 by merely scattering new sensors 12, for example, in an additional room of a home, in an automobile of the patient, or in the patient's 14 workspace in addition to their home. Likewise, these portable and disposable sensors 12 are easily collected or deactivated in order to reduce the size of the home environment 16. Sensors that are currently used in the art of remote patient monitoring are much too bulky to be "dusted" in such a way, and are too costly to be disposable. In addition, the sensors 12 are designed to be autonomous, such that they can automatically configure themselves with the rest of the sensor system 10. In other words, a new sensor 12 added to the system 10 will immediately communicate and coordinate with the other sensors 12 in the system 10 in order to detect what the other sensors 12 are sensing and whether that new sensor 12 should be activated or deactivated. In current remote patient monitoring systems, the patient must proactively turn on the sensor or apply the sensor every time information is collected, and often times, a single sensor is only intended and able to sense one particular sensing parameter.

In additional embodiments of the present invention, each new sensor 12 module comes with a software upgrade pack to automatically upload new processing capabilities into the central hub 18. Thus, the software platform of the central hub 18 is also modular-based, such that new upgrades can integrate with the existing features to enable a host of additional processing capabilities that utilize the integrated information. Thus, as soon as a new module is plugged into the system, the system automatically upgrades its overall processing capabilities to include the enhanced capabilities of the new module.

The system and method allows for the sensors to collect data for multiple sensing parameters at the same time, including such parameters as, but not limited to, ECG data, heart rhythm, partial pressure of oxygen, blood pressure, breathing quality, temperature, weight, activity levels, drug compliance, hydration and sleep habits. This information can then be integrated for analysis at the central hub. Table 1 illustrates particular sensors 12 in the system 10, their associated acquisition parameters, and whether those sensors 12 are configured to sense continuously for that acquisition parameter.

TABLE 1

| Sensor | Acquisition Parameter | Continuous? |
|---|---|---|
| ECG | waveform | yes |
| Heart rhythm | heart rate/pulse rate | yes |
| SpO$_2$ | partial pressure/oxygen saturation | yes |
| Blood Pressure | blood pressure | no |
| Breathing quality | breath rate/volume | no |
| Weight | kg | no |
| Activity Level | movement | yes |
| Drug Compliance | drug | no |
| Sleep Habits | multi-parameter (HR, breathing, etc.) | yes |
| Temperature | temperature | no |
| Fluid Balance | fluid concentration | yes |

The system and method of the present invention also allows the physician or clinician to remotely configure or reconfigure the parameters of the sensing system 10 such that on-demand medical diagnostics can be achieved from a remote location. The minimum requirements for realizing such a system 10 can be seen through the four basic components, including the sensors 12 used for gathering the physiological parameters from the patient 14. As stated previously, these parameters may include, but are not limited to, ECG signals, heart rhythm, partial pressure of oxygen, blood pressure, breathing quality, weight, temperature, activity levels, drug compliance, sleep habits, and fluid balance. The second basic component is the sensing sub-system 30, used for integrating the sensed information from its associated sensors 12 for a given function or application. The third basic component is the central hub 18, used for integrating and processing the data received by the sensing sub-systems 30. This component allows for multiple sub-systems 30 to be processed together for creating new and configurable applications. The central hub 18 also provides an interface for the patient 14 to interact or communicate with the clinician 26. The central hub 18 component is also used for storing the sensed data and processed results. The fourth basic component is the clinician hub 32, used for routing the sensed data and processed results to the respective clinicians 26 as necessary. This unit is also used as an access point that provides an interface for clinicians 26 to connect with the home environments 16 being monitored. Through this interface, the clinician 26 is able to access the home to reconfigure the sensing applications being monitored.

Figure 3A:
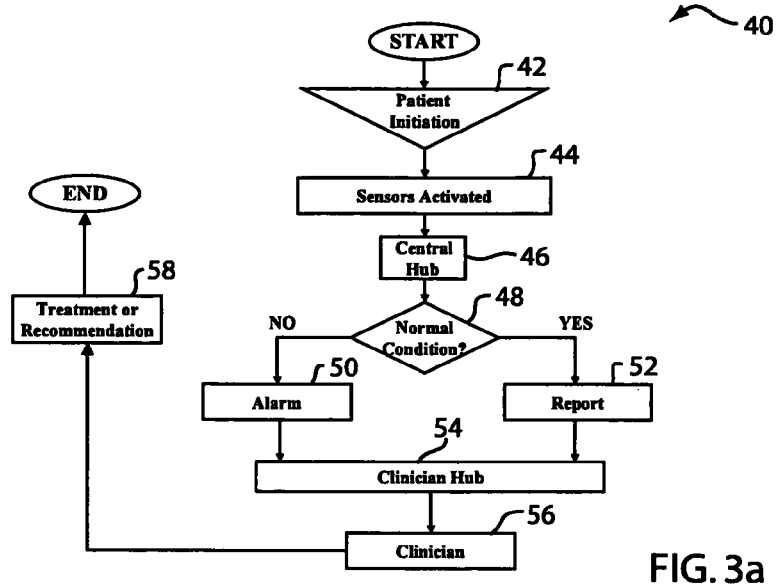
FIGS. 3a-3b illustrate a flow chart of an embodiment of the method of the present invention.

Referring to FIG. 3a, an embodiment of the monitoring method 40 is depicted. In step 42, the patient initiates the monitoring, and in step 44, the appropriate sensors are connected and activated. In step 46, the information collected from the sensors in step 44, is processed in the central hub. If the collected information is within a normal range, in step 48 a report 52 is issued to the clinician hub 54. If the information collected in step 44 indicates an abnormal condition, then in step 48 an alarm 50 is activated and sent to the clinician hub 54. In step 54, the clinician hub receives the report 52 or alarm 50, and processes this information and routes it to the appropriate clinician. In step 56, the clinician analyzes the alarm or report, and recommends treatment or another recommendation in step 58.

Figure 3B:
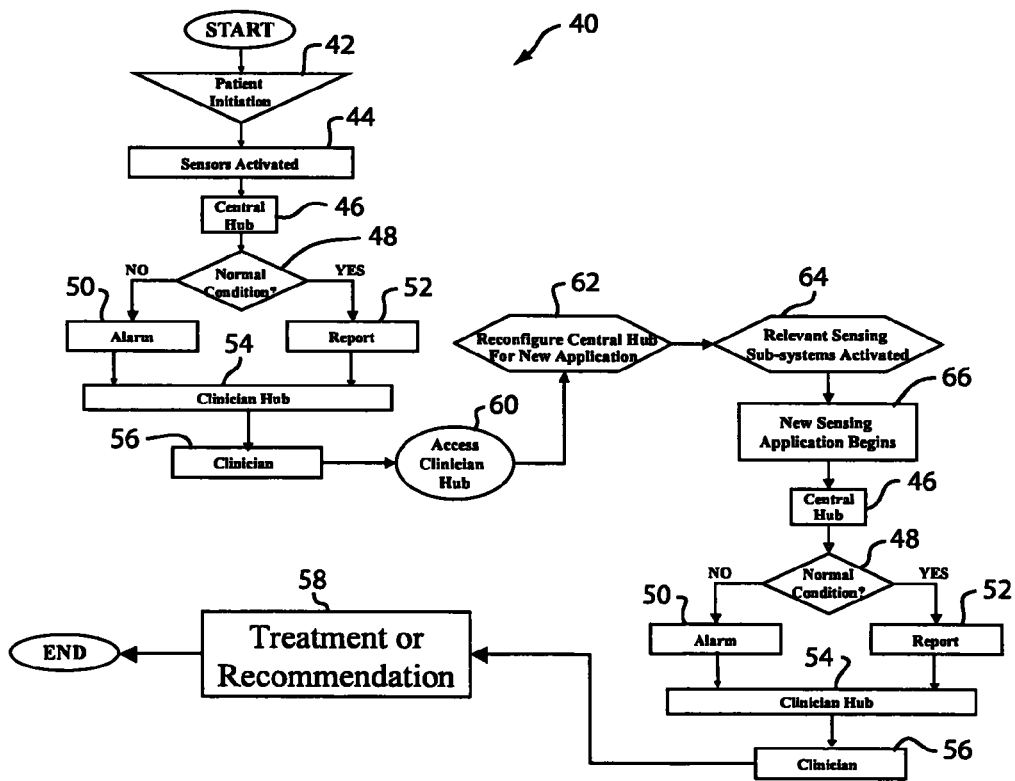

Referring to FIG. 3b, the monitoring method 40 may also include the ability for the clinician to reconfigure the sensing system to detect for new information through other parameters. In step 60, after the clinician receives the report or alarm from the clinician hub, the clinician may access the clinician hub, and in steps 62 econfigure the central hub, through the clinician hub for a new application. In step 64, the relevant sensing sub-systems are activated according to the new application, and in step 66, the new sensing application begins. The steps 46-58 then operate as indicated in the discussion of FIG. 3a.

Figure 4:
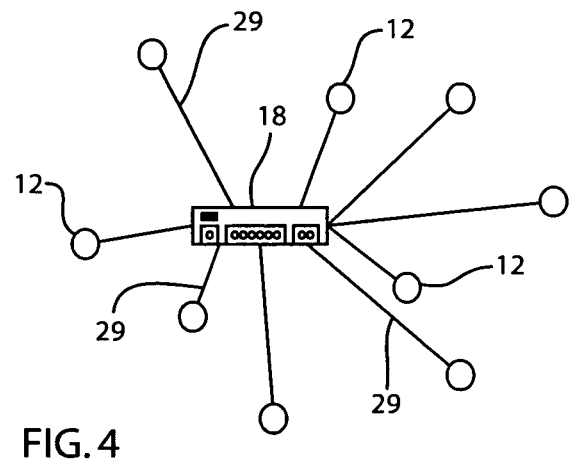
FIG. 4 illustrates a block diagram of an embodiment of the central hub of the present invention.

The system 10 includes an established wireless network whereby each sensor 12 is connected with each other wirelessly and is configured to communicate through the wireless network as depicted in FIG. 4. Each sensor 12 is also able to communicate to a central hub 18 through this wireless network 29. The network 29 may be configured where all sensors 12 connect and communicate directly with the hub 18, or it may be configured as an ad-hoc network 29 where each sensor 12 connects with another sensor 12 that bridges the connection to the central hub 18 (not shown).

Figure 5:
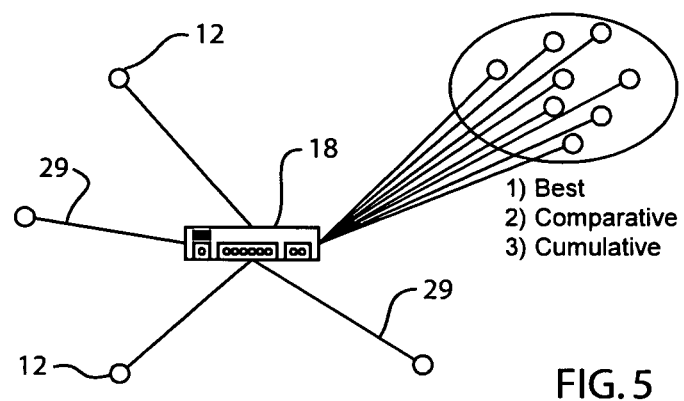
FIG. 5 illustrates a block diagram of an embodiment of the central hub of the present invention.

The system 10 consists of a central hub 18 or pre-processing center, whereby collected information from multiple sensors 12 is integrated and processed as shown in FIG. 5. This central hub 18 also provides an interface to either receive commands from the patient 14, or to send signals and/or directions to the patient 14. The pre-processing center 18 is also able to evaluate the data, e.g. as best, comparative, or cumulative, as shown, and perform operations on the sensed data. The result of the processing may trigger an action, such as, but not limited to, an alarm to the patient 14, an alert to the clinician 26, a treatment to the patient 14, a reminder to the patient 14, a report to the patient 14, a report to the clinician 26 or a report to an insurance agency.

Still referring to FIG. 5, multiple sensors 12 are able to coordinate with each other in an automated ad-hoc fashion to collect the relevant data for the relevant parameters. This includes the capability to turn on and off sensors 12, modify the sensing parameters, modify the sensor 12 sensitivity, or reconfigure the sensors 12. The sensors 12 continuously communicate with each other, and automatically establish communications connections with each other, as well as with the central hub 18, as long as the distance is within communication range.

Figure 6:
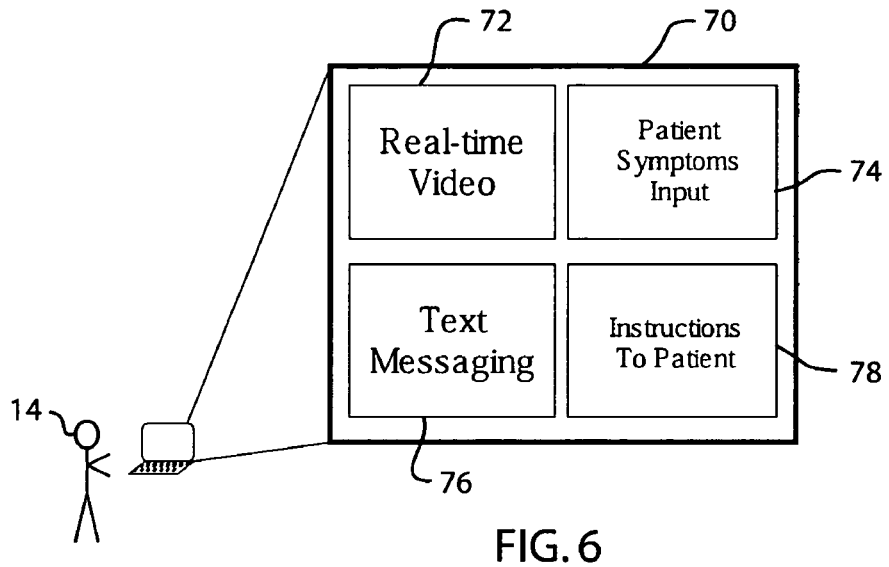
FIG. 6 illustrates a block diagram of an embodiment of a graphical patient interface of the present invention.

Referring to FIG. 6, the graphical patient interface 70 provides a means for the patient 14 to receive instructions, either from the clinician 26, or in an automated mechanism from the central hub 18. In a preferred embodiment, the graphical patient interface 70 includes a real-time video interface 72, a patient symptoms input interface 74, a text messaging interface 76 and an instructions to patient interface 78. Of course, in alternative embodiments, the graphical patient interface 70 may be configured by the patient 14 or the user 92 (FIG. 7) to meet specific needs of the system 10 and the clinican 26.

Figure 7:
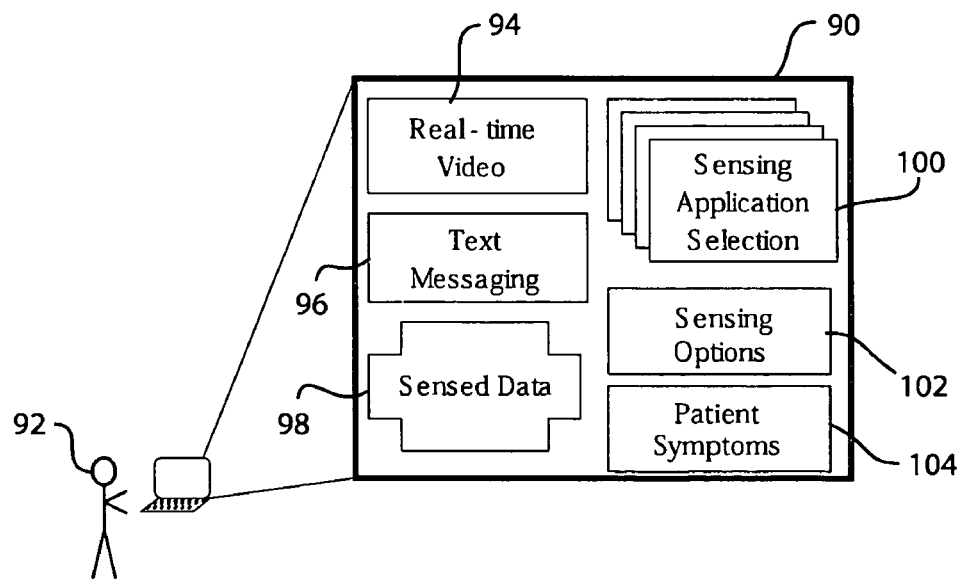
FIG. 7 illustrates a block diagram of an embodiment of a graphical user interface of the present invention.

Referring to FIG. 7, the graphical user interface 90 of the present invention is accessed by a user 92, preferably through a web-based server. In a preferred embodiment, the graphical user interface 90 includes a real-time video interface 94, a text messaging interface 96, a sense data interface 98, a sensing application selection 100, and a sensing module options interface 102 and a patient symptoms interface 104. In alternative embodiments, the graphical user interface 90 may be configured by the user 92 to meet the specific needs of the system 10 and the clinician 26.

Figure 8:
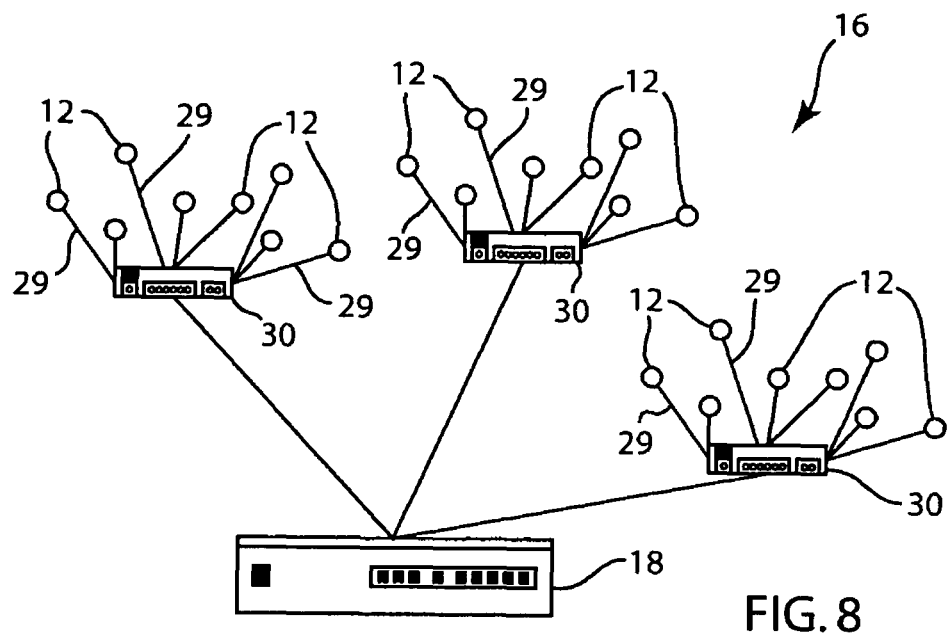
FIG. 8 illustrates a block diagram of an embodiment of the home environment system of the present invention.

Referring now to FIG. 8, the system 10 of the preferred embodiment includes a home environment 16 with a central hub 18, whereby collected information from multiple sensing sub-systems 30 is integrated and processed. The central hub 18 is able to evaluate and perform operations on the sensed data from the sensing sub-systems 30. The central hub 18 is configurable so that new sensing applications can be implemented by the system 10 when new hardware sensing sub-systems or new software processing algorithms are added to the system 10. Here, the clinician can configure the central hub 18 so that the monitoring of specific clinical applications can be added, deleted, or modified. The clinician is also able to configure the parameters of each sensor sub-system 30 through the central hub 18. This involves changing the sensitivity thresholds, sensing frequency, analysis procedures, or processing algorithms.

Still referring to FIG. 8, each sensing sub-system 30 can be considered a module, whereby it can be added or removed from the system 10 without compromising the performance of the other modules in the system 10. When a new module is added, it can be integrated into the existing network and effectively perform its sensing functions in an integrated fashion with the other modules. Each new sensor module comes with a software upgrade pack to upload new processing capabilities into the central hub 18. Thus, the software platform of the central hub 18 is also modular-based, such that new upgrades can integrate with the existing features to enable a host of additional processing capabilities that utilize the integrated information. Further, each sensor sub-system 30 is connected to a central hub 18 through a wireless network 29. The sensors 12 are able to communicate directly with the subsystem 30, and the subsystems 30 are able to communicate directly with the central hub 18 of the system 10 over the wireless network 29. The central hub 18 of the system 10 is then able to connect wirelessly to an external network of clinicians.

The central hub 18 of the system 10 is configured such that collected information from multiple sensors 12 and/or sensing sub-systems 30 is integrated and processed. This central hub 18 is able to evaluate and perform operations on the sensed data. The result of the processing may trigger an action, which includes but is not limited to: an alarm to the patient; an alert to the hospital or clinic; a treatment to the patient; a reminder to the patient; a report to the patient; a report to the hospital or clinic; and/or a report to an insurance agency.

Figure 9:
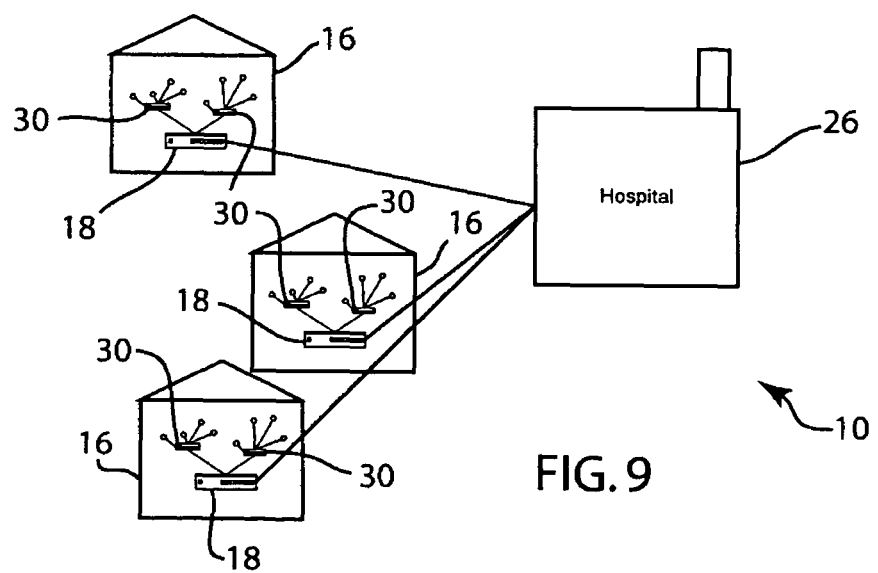
FIG. 9 illustrates a block diagram of an embodiment of the system of the present invention.

Referring to FIG. 9, the system 10 also includes a network of clinicians 26 that monitor the information sent from the remote patient monitoring system 10. The clinicians 26 may include various configurations. In a preferred embodiment, the central hub 18 may connect directly with a clinician 26 such as a hospital, as shown in FIG. 9. The clinicians 26 also provide a graphical user interface 90 (FIG. 7) that the clinician can access to configure or re-configure the central hub 18 for new applications. This interface 90 may be through a web-based server. An example of an implementation of the interface 90 was shown in FIG. 7.

The system 10 is to have secure data transfer by means of encryption, authentication, password registration, and permission control. The clinician is to have a password and be registered as an authorized user for the remote monitoring system of each patient for which clinician is providing care. The data being transferred between the remote patient and the clinician is not comprehensible by any third parties. The patient also has permission controls to modify only predetermined parameters of the remote sensing system.

The system 10 also includes secure data transfer by means of encryption, authentication, password registration, and permission control. The clinician 26 is to have a password and be registered as an authorized user 92 for the remote monitoring system 16 of each patient 14 for which clinician 26 is providing care. The data being transferred between the remote patient 14 and the clinician 26 is not comprehensible by any third parties. The patient 14 also has permission controls to modify only predetermined parameters of the remote sensing system.

The system 10 also includes a log file to record all prior system 10 operation. This log file may contain the patient's 14 sensed information, the configuration of the sensing sub-systems 30, the configuration of the central hub 18, the communication transcript between the patient 14 and the clinician 26, the diagnosis by the clinician 26, and any notes by either the patient 14 or the clinician 26.

Finally, the remote patient monitoring system 10 is also configured to perform general error checking and monitor system 10 integrity. This includes monitoring power failures, system diagnostics, patient interference or tampering, and sensor performance. When an error is identified, or the system integrity is outside specifications, an alarm is generated to the clinician 26 and patient 14.

The present invention allows for a more practical and more efficient system for monitoring the health of remote patients. Since the system is configurable, the sensing applications can easily be modified depending on the changing conditions of the patient and the discretion of the clinician. When a patient develops a new medical condition, new sensing applications can easily be integrated into the existing remote sensing system. Unnecessary sensing applications can also be removed from the sensing system based on the needs of the patient. The modular nature of the proposed system allows for this flexibility of sensing applications and parameters. The remote sensing system also provides several levels of processing capabilities, so that data received from the sensors can be pre-processed at the sensing sub-system, processed at the home processing hub, and further analyzed at the clinician hub before being sent to the hospital or clinician. This processing is configurable to the specific needs of each patient and can integrate data from multiple sensing sub-systems. The result is that multiple sensing parameters can be analyzed in relation with each other to provide an integrated and case-specific analysis, all while the patient remains at the home site.

The present invention has been described in terms of specific embodiments incorporating details to facilitate the understanding of the principals of construction and operation of the invention. Such reference herein to specific embodiments and details thereof is not intended to limit the scope of the claims appended hereto. It will be apparent to those skilled in the art that modifications maybe made in the embodiment chosen for illustration without departing from the spirit and scope of the invention.

The invention claimed is:

1. A system for remotely monitoring patient healthcare characteristics, the system comprising:
   a plurality of sensors in a home environment of a patient, wherein the plurality of sensors collect a set of patient health characteristics from a patient;
   a central hub located in the home environment, wherein the central hub controls the collection of the set of patient health characteristics and receives the set of patient health characteristics from the plurality of sensors, wherein the central hub determines whether the set of patient health characteristics is in a pre-determined range, send a patient status and generates a report and an alarm according to the determination;

a wireless network, wherein the wireless network couples the plurality of sensors and the central hub;

a clinician hub coupled with the central hub, wherein the clinician hub receives the patient status, the set of patient health characteristics, and any of the report and alarm generated from the central hub and sends the patient status and the set of patient health characteristics to an appropriate clinician, further wherein the clinician hub is configured to communicate with a plurality of central hubs in a plurality of home environments;

a graphical patient interface in the home environment, wherein the graphical patient interface allows the patient to activate the plurality of sensors, and further allows the patient to communicate with the clinician; and a graphical user interface at the appropriate clinician, wherein the graphical user interface allows the clinician to access the clinician hub and reconfigure the central hub, wherein the reconfiguring of the central hub allows the clinician to utilize a sensing application selection portion of the graphical user interface to select the set of patient health characteristics to be collected and further wherein reconfiguring includes, reconfiguring the graphical patient interface, and further allows the clinician to communicate with the patient.

2. The system as claimed in claim 1, wherein the size of the plurality of sensors are in a range from micro-scale to millimeter-scale.

3. The system as claimed in claim 2, wherein the plurality of sensors are any of a number of sensor types including: invasive implantable: non-invasive, portable device embeddable; and, non-invasive, home device embeddable.

4. The system as claimed in claim 1, wherein the clinician hub is located outside of the home environment.

5. The system as claimed in claim 1, wherein the patient status includes the report when the set of patient health characteristics is within a predetermined normal range, and the patient status includes the report and the alarm when the set of patient health characteristics are not in the predetermined normal range.

6. The system as claimed in claim 1, wherein the central hub is further configured to evaluate the set of patient health characteristics.

7. The system as claimed in claim 1, wherein each of the plurality of sensors is directly coupled with the central hub through the wireless network.

8. The system as claimed in claim 1, wherein the plurality of sensors are coupled with the central hub through the wireless network in an ad-hoc fashion.

9. The system as claimed in claim 1, further comprising a sensing sub-system configured to receive the set of patient health characteristics from the plurality of sensors, and further configured to relay the set of patient health characteristics to the central hub.

10. The system as claimed in claim 1, wherein the central hub is configurable by the clinician to change the set of patient health characteristics collected by the plurality of sensors.

11. A method of remotely monitoring patient healthcare characteristics, the method comprising:

activating a plurality of sensors, the plurality of sensors are activated with a graphical patient interface by a patient in a home environment;

collecting a set of patient healthcare characteristics from the patient with the plurality of sensors;

processing the set of patient healthcare characteristics in a central hub, wherein the plurality of sensors and the central hub are located in a home environment and the central hub controls the collection of the set of patient healthcare characteristics, and the central hub sends a patient status and the set of patient healthcare characteristics from the central hub to a clinician hub, further wherein the clinician hub is configured to communicate with a plurality of central hubs in a plurality of home environments;

directing the patient status with the clinician hub to an appropriate clinician; and accessing the patient status by the clinician with a graphical user interface wherein the graphical patient interface and the graphical user interface are configured to communicate with one another, and reconfiguring the central hub through the graphical user interface to choose the set of patient healthcare characteristics for collection, and reconfigure the graphical patient interface, wherein the central hub determines whether the set of patient health characteristics is in a pre-determined range and generates a report and an alarm according to the determination, and the patient status includes the report when the set of patient health characteristics is within a predetermined normal range, and the patient status includes the report and an alarm when the set of patient health characteristics are not in the predetermined normal range.

12. The method as claimed in claim 11, wherein the size of the plurality of sensors are in a range from micro-scale to millimeter-scale.

13. The method as claimed in claim 12, wherein the plurality of sensors are any of a number of sensor types including: invasive implantable; non-invasive, portable device embeddable; and, non-invasive, home device embeddable.

14. The method as claimed in claim 11, wherein the clinician hub is configured outside of the home environment.

15. The method as claimed in claim 11, further comprising evaluating the set of patient health characteristics.

16. The method as claimed in claim 11, wherein each of the plurality of sensors is directly coupled with the central hub through the wireless network.

17. The method as claimed in claim 11, wherein the plurality of sensors are coupled with the central hub through the wireless network in an ad-hoc fashion.

18. The method as claimed in claim 11, further comprising receiving the set of patient health characteristics from the plurality of sensors with a sensing sub-system, and further comprising relaying the set of patient health characteristics to the central hub with the sensing sub-system.

19. A remote monitoring system, comprising:

a plurality of sensors in a home environment of a patient, wherein the plurality of sensors collect a set of patient health characteristics from a patient;

a central hub in the home environment, wherein the central hub controls the collection of the set of patient health characteristics and receives the set of patient health characteristics from the plurality of sensors, wherein the central hub determines whether the set of patient health characteristics is in a pre-determined range, sends a patient status and generates a report and an alarm according to the determination;

a wireless network, wherein the wireless network couples the plurality of sensors and the central hub;

a clinician hub coupled with the central hub, wherein the clinician hub receives the patient status and the set of patient health characteristics from the central hub and sends the patient status and the set of patient health characteristics to an appropriate clinician, wherein the patient status includes the report when the set of patient health characteristics is within a predetermined normal range, and further wherein the patient status includes the report and an alarm when the set of patient health characteristics are not in the predetermined normal range, further wherein the clinician hub is configured to communicate with a plurality of central hubs in a plurality of home environments;

a graphical patient interface in the home environment, wherein the graphical patient interface allows the patient to activate the plurality of sensors, and further allows the patient to communicate with the clinician; and a graphical user interface at the appropriate clinician, wherein the graphical user interface allows the clinician to access the clinician hub and reconfigure the central hub, and further utilizes a sensing application selection portion of the graphical user interface to reconfigure the central hub to alter the set of patient health characteristics collected by the plurality of sensors, reconfigure the graphical patient interface and further allows the clinician to communicate with the patient.

* * * * *